US00PP32043P2

(12) United States Plant Patent
Pryce

(10) Patent No.: US PP32,043 P2
(45) Date of Patent: Aug. 4, 2020

(54) ***LAMPROCAPNOS* PLANT NAMED 'CUPID'**

(50) Latin Name: *Lamprocapnos spectabilis*
Varietal Denomination: CUPID

(71) Applicant: Matthew Pryce, Curve Lake (CA)

(72) Inventor: Matthew Pryce, Curve Lake (CA)

( * ) Notice: Subject to any disclaimer, the term of this patent is extended or adjusted under 35 U.S.C. 154(b) by 0 days.

(21) Appl. No.: 16/602,393

(22) Filed: Sep. 26, 2019

(51) Int. Cl.
*A01H 5/02* (2018.01)
*A01H 6/64* (2018.01)

(52) U.S. Cl.
USPC ..... Plt./426
CPC ..... *A01H 6/64* (2018.05)

(58) Field of Classification Search
USPC ..... Plt./426
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct *Lamprocapnos spectabilis* plant named 'Cupid' is disclosed, characterized distinctive light pink flowers, light green foliage and bushy plants. The new variety is a *Lamprocapnos spectabilis*, suitable for outdoor landscape and container use.

2 Drawing Sheets

Latin name of the genus and species: *Lamprocapnos spectabilis.*

Variety denomination: 'CUPID'.

BACKGROUND OF THE INVENTION

The new cultivar is the result of a chance discovery in a garden in Curve Lake, Ontario, Canada. The inventor Matthew Pryce, discovered the new variety as a naturally occurring chance seedling growing in a garden of the parent variety, an unnamed, unpatented *Lamprocapnos spectabilis*. The discovery was made during 2014.

After selecting and isolating the new cultivar, asexual reproduction of the new cultivar 'CUPID' was first performed by division during the Fall of 2014, in Curve Lake. 'CUPID' has since produced several generations through asexual propagation and has shown that the unique features of this cultivar are stable and reproduced true to type.

SUMMARY OF THE INVENTION

The cultivar 'CUPID' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CUPID'. These characteristics in combination distinguish 'CUPID' as a new and distinct *Lamprocapnos* cultivar:

1. Light pink flower.
2. Distinctive light green foliage.
3. 2 cm flower diameter.

PARENTAL COMPARISON

Plants of the new cultivar 'CUPID' are similar to the parent, in most horticultural characteristics. However, 'CUPID' differs in having a distinctive light pink flower color, compared to the dark pink flower of the parent variety. Additionally, the new variety forms a bushier plant than the parent variety.

COMMERCIAL COMPARISON

Plants of the new cultivar 'CUPID' can be compared to the commercial variety *L. spectabilis* 'Alba'. Plants of these two cultivars are similar in most horticultural characteristics. However, the new variety 'CUPID' has light pink flowers whereas this comparator has white flowers.

BRIEF DESCRIPTION OF THE PHOTOGRAPHS

Figure 1:
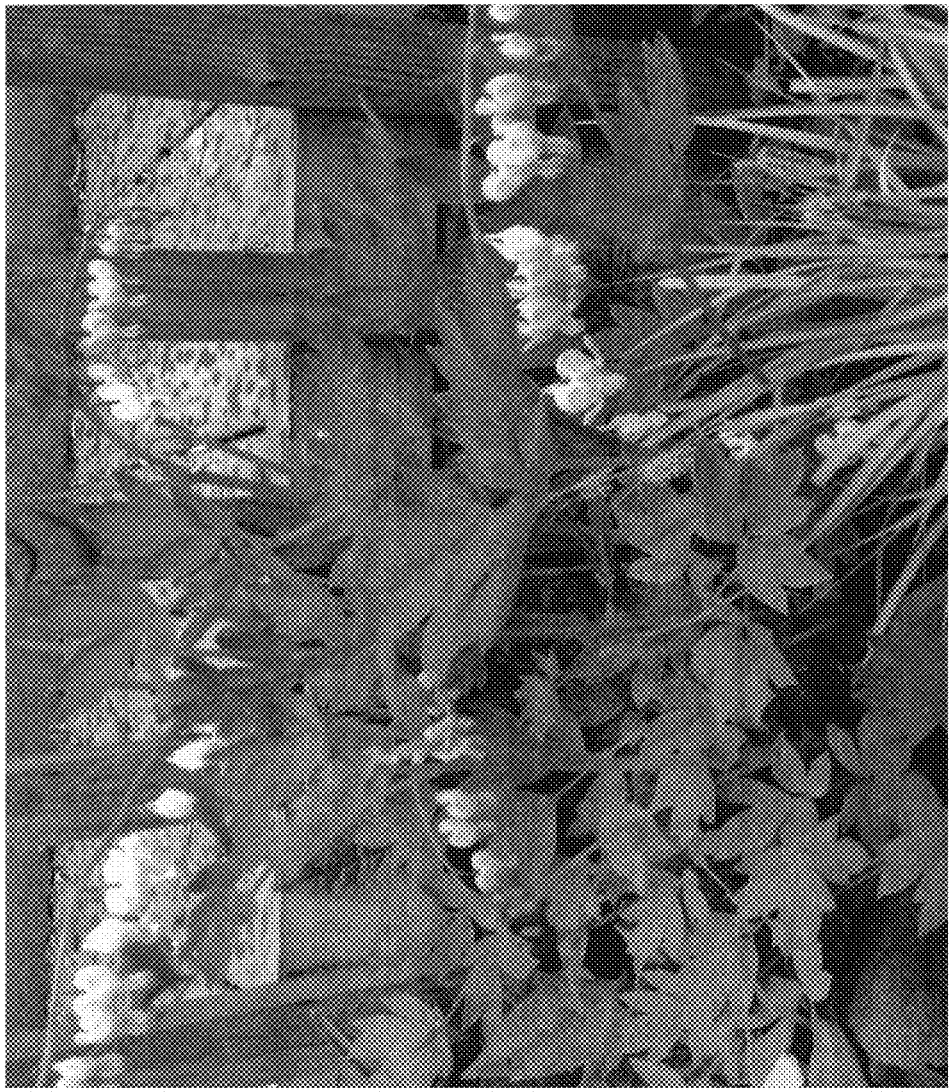

The accompanying photograph in FIG. 1 illustrates in full color a typical plant of 'CUPID' grown outdoors in Ontario, Canada. This plant is approximately 1 year old.

Figure 2:
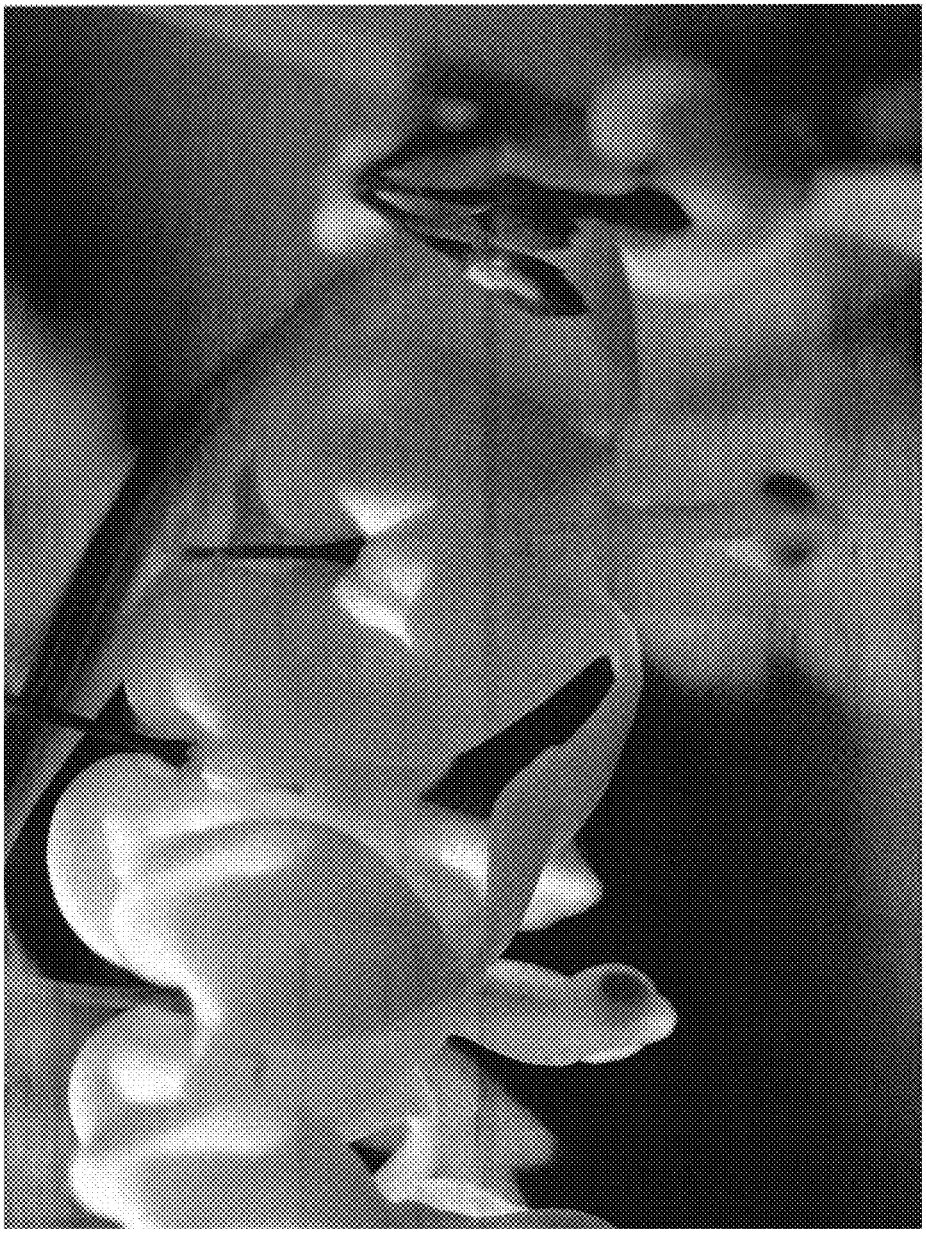

FIG. 2 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CUPID' plants grown outdoors in the Netherlands. Temperatures ranged from Approximately −10° C. to 30° C. day and night. No artificial light, photoperiodic treatments or chemical treatments were given to the plants. Measurements and numerical values represent averages of typical plant types.

Botanical classification: *Lamprocapnos spectabilis* 'CUPID'.

Age of the plant described: Approximately 18 months.

Container size of the plant described: 17 cm commercial container.

DETAILED BOTANICAL DESCRIPTION

Propagation

Time to initiate roots: Typically propagated outdoors, from March to May. Root initiation takes approximately 10 days, with full rooting within 14 days.

Root description: Moderately dense, thin, slightly fleshy, slightly fibrous, colored near RHS Grey-Brown 199D.

Plant

Growth habit: Broad, orbicular flowering perennial.

Pot size of plant described: 17 cm.

Height: Average: 50 to 60 cm.

Plant spread: Average: 60 to 70 cm.

Growth rate: Moderate.

Branching characteristics: Basal branching with stem leaves and axillary and terminal racemes.

Length of primary lateral branches: Average: 40 to 50 cm.

Quantity of primary lateral branches: Average: 12.

Characteristics of primary lateral branches:

- *Form*.—Rounded, slightly angled.
- *Diameter*.—Average: 0.5 cm.
- *Color*.—Near RHS Green 143C.
- *Texture*.—Smooth.
- *Strength*.—Moderate.

Internode length.—Average 3 cm.

Foliage

Leaf:

- *Arrangement*.—Alternate.
- *Shape*.—Compound, biternate (broad ovate in outline).
- *Quantity*.—Approximately 5 to 9 per branch.
- *Average length*.—15 to 19 cm.
- *Average width*.—7 to 10 cm.

Individual leaf blades (leaflets):

- *Average length*.—5 to 6 cm.
- *Average width*.—3 cm.
- *Shape of blade*.—Trifoliate (obovate to orbicular in outline).
- *Apex*.—Acute.
- *Base*.—Cordate.
- *Margin*.—Entire to irregularly and sparsely serrate.
- *Texture of top surface*.—Smooth.
- *Texture of bottom surface*.—Smooth.
- *Aspect*.—Leaf blades slightly concave.
- *Color*.—Young foliage upper side: Near RHS Yellow-Green 144B. Young foliage under side: Near RHS Yellow-Green 145A. Mature foliage upper side: Near RHS Green 143B. Mature foliage under side: Near RHS Green 143C. Venation: Type: Pinnate. Venation color upper side: Near RHS Yellow-Green 144C. Venation color under side: Near RHS Yellow-Green N144C.
- *Petiole*.—Length: Average range 7 to 11 cm. Diameter: Average 0.3 cm. Color: Near RHS Yellow-Green 144C. Texture: Smooth.

*Stipule description* (*if present*).—No stipules present.

Inflorescence

Natural flowering season: Approximately April through June in Ontario, Canada.

Inflorescence and flower type and habit: Individual flowers in axillary and terminal racemes.

Inflorescence dimensions:

- *Height*.—Average 5 cm.
- *Length*.—Average range 10 to 14 cm.

Rate of flower opening: 5 to 8 days from bud to fully opened flower.

Flower longevity on plant: Average one week.

Persistent or self-cleaning: Self-cleaning.

Bud:

- *Shape*.—Obovate.
- *Length*.—1.0 cm.
- *Diameter*.—0.3 cm.
- *Color*.—Near RHS Yellow-Green 145A.

Flower size:

- *Diameter*.—At widest: 2.1 cm; at narrowest: 0.8 cm.
- *Depth*.—2.0 cm.
- *Aspect*.—Pendulous.
- *Flowers per inflorescence*.—Average range 3 to 8.

Petals:

- *Quantity*.—4.
- *Arrangement*.—2 oppositely placed pairs of similar petals.
- *Length*.—Two narrowest petals average: 2.0 cm. Two widest petals average: 2.0 cm.
- *Width*.—Narrowest petal average: 0.3 cm. Widest petal average: 1.0 cm.
- *Shape*.—Narrowest petals lanceolate, fused at the tips. Widest petals orbicular, but folded.
- *Apex*.—All petals have an acute apex.
- *Base*.—All petals have a cuneate base.
- *Margin*.—Entire.
- *Texture, upper and lower surfaces*.—Dull, smooth, non-pubescent.
- *Color*.—When opening, upper surface: Narrowest petal; Near RHS White N155D, base near RHS Red 53A. Widest petal; near RHS Red 38D, tip darker; 38B, outer tip Orange 27D. When opening, lower surface: Narrowest petal; Near RHS White N155D, base near RHS Red 53A. Widest petal; near RHS Red 38D, tip darker; 38B, outer tip Orange 27D. Fully opened, upper surface: Narrowest petal; RHS Yellow 11D, base RHS Red 46A. Widest petal; RHS Red 56C flushed 55D. Fully opened, lower surface: Narrowest petal; RHS Yellow 11D, base RHS Red 46A. Widest petal; RHS Red 56C flushed 55D.

Bracts (if present): No bracts present.

Sepals: No separate petals and sepals present, only petals (see above).

Peduncles:

- *Length*.—Average range 9 to 12 cm.
- *Diameter*.—0.2 cm.
- *Angle*.—About 75° to the lateral branch.
- *Strength*.—Moderate.
- *Texture*.—Smooth.
- *Color*.—Near RHS Green 143C.

Pedicels:

- *Length*.—1.0 cm.
- *Diameter*.—1 mm.

*Strength*.—Moderate.

*Texture*.—Smooth, dull due to a waxy layer.

*Color*.—Near RHS Green 143C.

Fragrance: No fragrance.

Reproductive Organs

Stamens:

*Number*.—6, fused in two groups of three, one on each side of the ovary, covered by the two narrowest petals.

Anthers:

*Shape*.—Anthers basifixed, narrow oblong, filament curved, following the shape of the narrowest petals.

*Length*.—Anthers approximately 0.1 cm. Filaments approximately 2.0 cm.

*Color*.—Anther: Near RHS Yellow 7A. Filaments: Near RHS Red 56B.

*Pollen*.—Color: Near RHS Yellow 7B. Quantity: Moderate.

Pistil:

*Number*.—1.

*Length*.—2.0 cm.

*Style*.—Length: 1.0 cm. Color: Near RHS Yellow-Green 145C.

*Stigma*.—Shape: Umbraculate. Color: Near RHS Yellow-Green N144B. Ovary Color: Near RHS Yellow-Green 145A.

Other Characteristics

Seeds and fruits: Not observed to date.

Disease/pest resistance: Neither resistance nor susceptibility to normal diseases and pests of *Lamprocapnos* has been observed.

Temperature tolerance: USDA Zones 3-9.

What is claimed is:

1. A new and distinct cultivar of *Lamprocapnos* plant named 'Cupid' as herein illustrated and described.

* * * * *